(12) United States Patent
McGee

(10) Patent No.: US 6,719,793 B2
(45) Date of Patent: *Apr. 13, 2004

(54) METHOD OF RESTRUCTURING BONE

(75) Inventor: Thomas D. McGee, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/104,063

(22) Filed: Mar. 25, 2002

(65) Prior Publication Data

US 2002/0147451 A1 Oct. 10, 2002

Related U.S. Application Data

(62) Division of application No. 09/379,608, filed on Aug. 24, 1999, now Pat. No. 6,364,909, which is a continuation-in-part of application No. 09/146,333, filed on Sep. 2, 1998, now Pat. No. 6,312,467, which is a continuation of application No. 08/682,150, filed on Jul. 17, 1996, now abandoned.

(60) Provisional application No. 60/001,481, filed on Jul. 18, 1995, and provisional application No. 60/003,407, filed on Sep. 8, 1995.

(51) Int. Cl.[7] ................................................. A61F 2/28
(52) U.S. Cl. .................................. 623/16.11; 623/23.56
(58) Field of Search .................. 606/62, 86; 623/18.11, 623/16.11

(56) References Cited

U.S. PATENT DOCUMENTS

| 3,710,789 A | | 1/1973 | Ersek |
| 3,787,900 A | * | 1/1974 | McGee ........................ 424/422 |
| 3,849,805 A | | 11/1974 | Leake et al. |

(List continued on next page.)

OTHER PUBLICATIONS

Niederauer et al.; "Attachment of epithelial cells and fibroblasts to ceramic materials"; Biomaterials 1994 vol. 15, No. 5, pp. 343–352.

Tweden et al.; "Evaluation of the Tissue Response of Organic, Metallic, Ceramic and Osteoceramic Tooth Roots"; materials Science Forum vol. 293 (1999) pp. 17–36.

Thomas D. McGee et al.; "A Machinable Biologically–Active Composite as a Guide for Diaphysis Regeneration"; Presented at the International Symposium Advanced Materials for Orthopedic Applications, NIST, Jun. 8, 1999.

Thomas D. McGee et al., "A Biologically Active Ceramic Material with Enduring Strength"; Encyclopedic Handbook of Biomaterials and Bioengineering, vol. 2, Part A (Materials), pp. 1413–1427.

Thomas D. McGee et al.; "General Requirements for a Successful Orthopedic Implant"; Encyclopedic Handbook of Biomaterials and Bioengineering, vol. 1, Part B (Applications), pp. 69–82.

*Primary Examiner*—Cary E. O'Connor
*Assistant Examiner*—Candice C. Melson
(74) *Attorney, Agent, or Firm*—Dickstein Shapiro Morin & Oshinsky

(57) ABSTRACT

A method of producing reconstructed bone. The method includes providing an implant structure having a calcium phosphate component, and stabilizing the implant adjacent the healthy bone until tissue can recover, bond to the implant and support the normal required loading. The implant structure provides morphological continuity and anatomical contact between the implant body and the adjacent healthy bone. The method further includes providing for physiological processes to maintain a healthy junction between the implant and the healthy bone. The method further includes controlling, guiding and directing the bone reconstruction process in surgical situations where healthy recovery would not otherwise occur.

4 Claims, 5 Drawing Sheets

U.S. PATENT DOCUMENTS

| | | |
|---|---|---|
| 3,906,550 A | 9/1975 | Rostoker et al. |
| RE33,161 E | 2/1990 | Brown et al. |
| RE33,221 E | 5/1990 | Brown et al. |
| 4,938,768 A | 7/1990 | Wu |
| 4,960,426 A | 10/1990 | Atsumi |
| 5,112,354 A | 5/1992 | Sires |
| 5,147,361 A | 9/1992 | Ojima et al. |
| 5,211,661 A | 5/1993 | Shinjou et al. |
| 5,211,664 A | 5/1993 | Tepic et al. |
| 5,281,226 A | 1/1994 | Davydov et al. |
| 5,443,483 A | 8/1995 | Kirsch |
| 5,503,164 A | 4/1996 | Friedman |
| 5,676,699 A | 10/1997 | Gogolewsk et al. |
| 5,693,099 A | 12/1997 | Harle |
| 6,454,810 B1 * | 9/2002 | Lob .................. 623/23.47 |

\* cited by examiner

METHOD OF RESTRUCTURING BONE

This application is a divisional of U.S. application Ser. No. 09/379,608, filed Aug. 24, 1999 U.S. Pat. No. 6,364, 909, which is a continuation-in-part of U.S. application Ser. No. 09/146,333, filed Sep. 2, 1998 U.S. Pat. No. 6,312,467, which is a continuation of U.S. application Ser. No. 08/682, 150, filed Jul. 17, 1996, now abandoned, which claims priority to U.S. Provisional Application No. 60/001,481, filed Jul. 18, 1995 and Ser. No. 60/003,407, filed Sep. 8, 1995.

FIELD OF THE INVENTION

This invention relates to a method of producing restructured bone, and more particularly to a method causing bone to bond to an implant containing a calcium phosphate component, and a method to control the restructuring of bone through the use of an implant containing calcium phosphate.

BACKGROUND OF THE INVENTION

The need for bone implants, joint replacements, and regrowth of missing or damaged bones is great because of bone damage due to accidents, cancer surgery and genetic defects. The ideal permanent bone implant would be compatible with living tissue and would be able to withstand the stresses typically placed upon bones during normal movement. Such an implant has proved difficult to develop, however.

Most materials when used in vivo cause tissue reactions such as inflammation, the presence of macrophages, a fluid filled capsule, and a fibrous tissue covering. Only a few materials are sufficiently inert in the body to be used for prostheses. Even the bio-inert materials are walled-off by a fibrous capsule. For allergic individuals one or more of the undesirable responses above may occur. The fibrous capsule allows some movement to occur as it develops. This can cause movement that is accommodated by a thicker capsule, which allows even more movement, which creates an even thicker capsule and leads, progressively, to failure.

Another problem with bone implants is their uniform structure that does not match the inherent non-uniformity of bone. This, and the difference in elastic properties between the implant and the bone, can lead to problems of stress distribution in the bone. High local stresses cause bone resorption and low local stresses lead to osteoporosity and weak bone.

Joint replacements are in high demand, especially for hips and knees. Approximately 250,000 total hip replacements are performed in the United States each year. Approximately 25,000 revisions are also performed each year because the failure rate is about 10%, although many surgeons expect a 12 to 15 year prosthesis life. This high failure rate has many causes. The most common is pain and loosening under stress. This is usually aseptic loosening and has several underlying causes. These include bone deterioration at the bone/implant interface and inflammation at the joint capsule as the result of particulate debris from the polymethylmethacrylate ("PMMA") cement or from wear of polyethylene or metal components. Some prostheses use polycrystalline aluminum oxide as one or more of the articulating components to reduce wear debris. The use of polycrystalline aluminum oxide is very expensive because of the complex shapes in use and the brittle nature of the material. Single crystal aluminum oxide in the form of sapphire or ruby has even less wear. Another cause of failure is the use of PMMA cement to anchor the prosthesis in such a way that the trabeculae of porous bone become filled with cement, which blocks the blood supply needed for bone repair and limits the life of the implant.

The number of bone replacement surgeries is expected to increase because patients are living longer, and the number of older people in the population will increase dramatically in the next two decades. Other joints such as elbows and shoulders also require replacements, which are being conducted at an increasing rate.

Joint replacements that are compatible with native bone tissue would have increased lifetimes and improved functioning. Problems with current hip replacements include the need to remove the ball and stem of the femur to accommodate typical prostheses, and the use of tissue-incompatible materials such as polyethylene, metal, and polymethylmethacrylate cements. Typical methods of replacing joints may also cause problems because of excessive reaming of the acetabulum, which should be avoided because it causes problems in the event of future replacements.

Bone regrowth is often desired when the native bone tissue is missing or is damaged, especially in circumstances in which an implant would not be feasible. In addition to human circumstances this may include repair of hollow bones such as avian bones, or repair of damage to the long bones of some mammalian species such as dogs and cats, which does not normally occur if the length of missing bone is more than 1½ times the external diameter of the bone. Typically bone regrowth is encouraged by removing bone from either the patient or another individual and grafting it in the damaged site, but such bone grafting is complicated, involves multiples surgeries, and if allogenic bone is used there may be problems of infection or rejection of the graft. Bone substitutes have been used, but typically lack tissue compatibility and may produce undesirable foreign body response, especially if they release particulates due to friction or chemical reactions.

Typical materials used for implants, joint replacements, artificial bone grafts, and fixation devices such as bone screws and posts include metals such as titanium, 316-L stainless steel, A16V4 titanium, and cobalt-chrome alloys, organic materials such as very high molecular weight (VHMW) polyethylene and polymethylmethacrylate, and ceramics such as alumina and zirconia. Although these materials are bioinert, and have minimum solubility in tissue fluids, they all invoke a foreign body response to some degree, and none of them are bonded directly by osseous tissue. Over time, movement of the implant causes the fibrous capsule to thicken, which causes tissue degeneration, leading to more movement and progressive failure of the implant. Other problems with these materials include excessive wear and particularization of metal and organic materials, and the brittleness of typical ceramics.

Attempts to avoid or lessen capsule formation, which is the major cause of implant and replacement failure, include the use of hydroxyapatite coatings, or metal beads or mesh to encourage tissue ingrowth into the implant or other orthopedic device. Joint replacements are often fixed into place with polymethacrylate cement that is in contact with the osseous tissue. Cement is inserted under pressure before the prosthesis component is inserted to ensure that the cement fills the space between the prosthesis and the tissue. The insertion of cement into trabecular bone penetrates and displaces the soft tissue in the trabeculae, effectively shutting off the blood and nutrient avenues for repair of the trabecular walls and leading to progressive tissue degeneration.

Materials that are not inert but are not walled off by a foreign-body capsule have especially desirable tissue response. The only crystalline materials of this nature are calcium phosphates such as hydroxyapatite [$Ca_{10}(PO_4)_6(OH)_2$], fluorapatite, oxyapatite, tricalcium phosphate [$Ca_3(PO_4)_2$], and calcium pyrophosphate [$Ca_2P_2O_7$]. The natural mineral in bone is impure hydroxyapatite, which contains water, but ceramics typically have less water due to the high temperature firing processes used to make them. The tissue response for ceramics with calcium-to-phosphorous ratios between 1.0 and 2.0 is known to be suitable for hard tissue.

Calcium phosphate materials are often called osteoconductive, meaning that they stimulate bone growth, as opposed to osteoinductive, which refers to the production of osseous tissue in soft tissue sites. The lack of a fibrous capsule and the ability of bone to bond directly to the calcium phosphates makes them very interesting for prosthesis applications. Tissue response is critical, and if calcium phosphates can be used to achieve a bond between the implant and the native hard tissue, they make long implant life a possibility.

The calcium phosphates are brittle materials. Brittle materials fail as the result of stress concentration resulting from flaws present in the material. Reducing the flaws in manufacturing improves the mechanical strength. Thus it is possible to produce strong calcium phosphates such as tricalcium phosphate and hydroxyapatite. Unfortunately, their bioactivity allows the surface to react with the surrounding tissue, introducing new flaws. Therefore, even if made strong before implanting they are not strong shortly after implanting. This is true for the crystalline ceramic phosphates and for glasses containing calcium phosphate. This is an inherent weakness that has been overcome by introducing a second phase to form a composite identified herein as an osteoceramic, and disclosed more fully in U.S. Pat. No. 3,787,900, issued to McGee, and herein incorporated by reference. The osteoceramic has enduring strength and has the necessary calcium phosphate components for tissue bonding.

Osteoceramics are composites of calcium phosphates with strong, inert ceramic materials, such as magnesium aluminate spinel ($MgAl_2O_4$). To achieve fine distribution and interconnection of the calcium phosphate compound in the osteoceramic, at least 25%, and preferably 50% of the ceramic volume should be calcium phosphate.

What is needed is a method of inducing damaged bone to repair itself by incorporating a prosthetic device or bone guide into the skeletal structure of a human or animal. Also needed is a method of incorporating a joint replacement device into the skeletal structure of a human or animal.

SUMMARY OF THE INVENTION

The present invention provides a method of inducing damaged bone to repair itself. The method includes providing an osteoceramic implant, placing the implant either adjacent to a damaged bone or between two portions of damaged bone, and stabilizing the implant adjacent the damaged bone until the bone tissue can regrow. In a preferred embodiment the implant is designed so that bone tissue may bond directly to the osteoceramic implant, which has a bulk geometry, to allow bone to interlock into the prosthesis and a surface geometry configured to match the surface geometry of the damaged bone. A second preferred embodiment provides a method of inserting a guide containing calcium phosphate into the intramedullary cavity of the damaged bone and inducing the growth of bone tissue along the guide.

Also provided is a method of incorporating a joint replacement device into the skeletal structure of a human or animal, wherein the device has osteoceramic portions that contact the native bone tissue of the human or animal and the native bone tissue bonds to the osteoceramic. Preferred embodiments include an elbow replacement device and a hip replacement device. In a particularly preferred embodiment, the present invention provides a method of replacing bone in the skeletal structure of a human or animal to induce repair of a portion of damaged bone and bond the damaged bone tissue to the new tissue replacement. This method is performed by providing a tissue replacement prosthesis composed of a biologically-active ceramic composite, e.g., an osteoceramic containing calcium phosphate and having enduring strength, and providing a prosthesis geometry to ensure that physical stresses in the adjacent damaged tissue are similar to those of natural bone at the implant site. Openings, such as holes, notches, grooves and splines, are also provided in the prosthesis into which bone can grow to anchor the prosthesis. These openings are preferably large enough to establish strong, healthy bone in the openings, and have a geometry for tissue ingrowth such that the blood and lymph systems normally present can operate freely to support new healthy replacement bone in said openings. In addition, the surface geometry of the prosthesis is provided with a geometry similar to the surface geometry of a cut section of bone at the implant site. The replacement prosthesis is then positioned in contact with adjacent bone, and the prosthesis is stabilized for a sufficient time for said new bone to bond to said prosthesis. The prosthesis maybe in the shape of a hollow osteoceramic cylinder for the repair of the diaphysis of long bones. The prosthesis may also be used to repair the extremities of a long bone, or for an articulating joint, in which the prosthesis serves as the interface between the tissue and the metal, ceramic or plastic components of a functioning prosthesis. The prosthesis may also be inserted in a defect in laminar bone with provision for bone ingrowth into openings from the internal blood supply layer between the external cortices of said laminar bone.

Additional advantages and features of the present invention will be apparent from the following detailed description, drawings and examples which illustrate preferred embodiments of the invention.

DETAILED DESCRIPTION OF THE PREFERRED EMBODIMENTS

Reference will now be made in detail to the presently preferred embodiments of the invention, which together with the drawings and the following examples, serve to explain the principles of the invention. These embodiments are described in sufficient detail to enable those skilled in the art to practice the invention and it is to be understood that other embodiments may be utilized, and that structural and biological changes may be made without departing from the spirit and scope of the present invention.

The term "osteoceramic" used in the following description refers to a composition comprising ceramic materials such as magnesium aluminate spinel ($MgAl_2O_4$) and calcium phosphates such as hydroxyapatite, fluorapatite, oxyapatite, tricalcium phosphate or calcium pyrophosphate, as is described in U.S. Pat. No. 3,787,900, which is incorporated herein by reference.

The present invention concerns methods of successfully inducing damaged bone to repair itself by incorporating an implant into the skeletal structure of a human or animal. Also within the scope of the present invention are methods of incorporating a joint replacement device into the skeletal structure of a human or animal for articulably connecting a first and second bone. The term "joint" as used herein shall be understood to mean any connection of bone ends or one bone to another via an articulable surface, including, but not limited to, hips, elbows, knees, shoulders, and spine, etc.

It has long been known that the structure of bone is determined by the loads applied, and that bone remodels to support loads (Wulff's law). Internal fixation, such as a bone plate with screws, is often needed for a bone graft. When a plate is used the rigidity of the plate prevents micromotion adjacent to it. Opposite the plate, because of bending under load micromotion, microstrain increases proportional to the distance away from the stabilizing plates. Microstrain excites the physiological responses, such as proliferation of osteoblasts, that are needed for bone generation. Microstrain must be controlled for a bone graft to be successful. A gradual transfer of mechanical load from the bone plate to the new bone must be accomplished. If the graft is in a proper position it may be incorporated into the new bone to carry part of the mechanical load. New bone is wavy in structure, and later remodels to a structure appropriate to the structure of the surrounding bone. During and after the transition the graft may or may not carry load if the supporting bone is strong enough. Ultimately, a successful graft will have remodeled bone suitable to the strength required by the loads imposed. This remodeling shifts the load from the bone plate to the remodeled bone. Ultimately the bone plate can be removed.

Long Bone Repair: Tissue Bonding to the Implant

Figure 1:
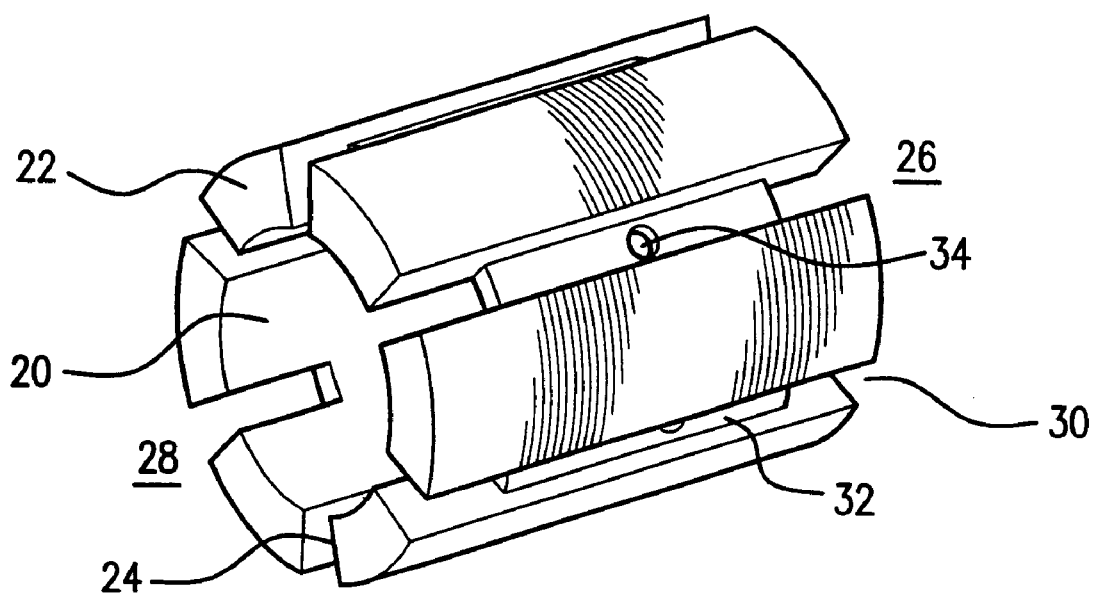
FIG. 1 is a perspective view of the bone bridge implant used in the method of the present invention.
Figure 2:
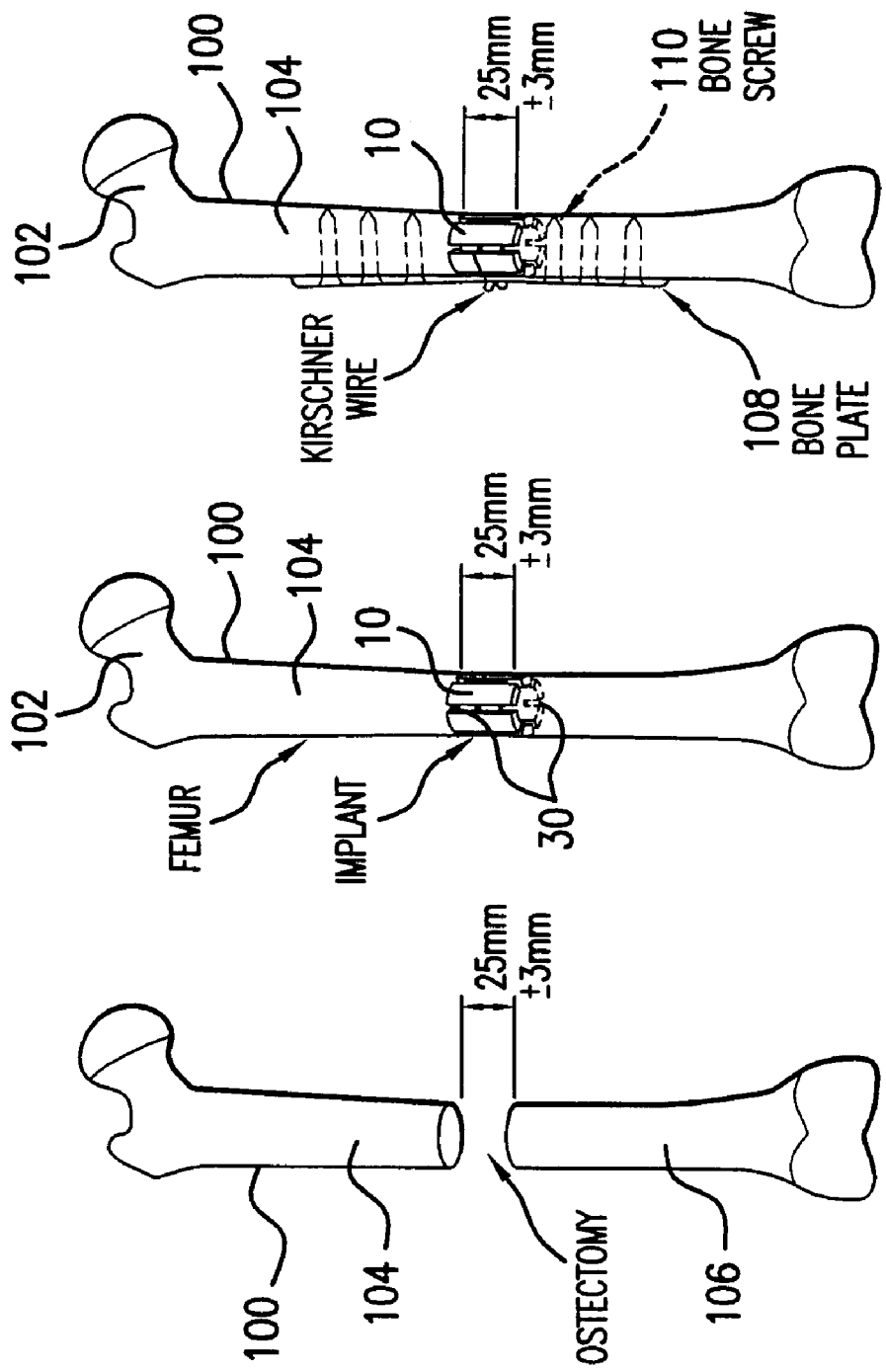
FIGS. 2A, 2B, and 2C are a series of front elevational views of a femur illustrating a surgical procedure used in the present invention.

Referring now to the drawings, a bone bridge prosthetic device 10, shown in FIG. 1, for inducing bone repair of a portion of a damaged long bone is shown in FIGS. 2A, B and C. The bone bridge 10 comprises a hollow osteoceramic cylinder 20 having an outer surface 22. The outer surface 22 has a surface geometry configured to match the surface geometry of the damaged bone, e.g., if the bone bridge 10 is to be used adjacent to trabecular bone, the outer surface 22 will have a plurality of web-like projections (not shown) thereon.

Example 1 below demonstrates a method of making hard tissue bond to an implant, so that the implant is functional as the result of bone bonding, rather than mechanical fixation. Temporary fixation is, of course, required so that the wound healing and remodeling necessary for tissue bonding can take place. However, after bonding has taken place the temporary supports can be removed. The replacement of a section of a long bone is used here to discuss the principles involved. We will consider a "bone bridge" replacement of a section of a dog's femur.

As shown in FIGS. 2A, 2B and 2C, the diaphysis of the femur 100 of a dog is in the shape of a tube, slightly curved. The cortical bone of the femur 100 is thin. The forces imposed on the femur 100 are compressive, bending, tensile, and rotation. Because of the offset neck 102 of the femur, important bending forces put the femur 100 in tension laterally and in compression medially. A prosthesis put into place must withstand these forces; but, more importantly, the bond of the tissue to the implant must also be strong enough to withstand these forces. The structure of the tissue implant interface must be adjusted to achieve this. When no implant is in place the continuous remodeling of mature bone, which is known to be stress regulated, maintains the femur shape and thickness. Any implant, then, should produce the same field of stresses as the natural bone. This dictates the nature of the contact between the bone and the implant. The resolved areas of contact for the implant should be the same or nearly the same as the area would be if bone were present instead of the implant. The structure of the implant in contact with the bone should encourage bone bonding.

The surgical procedure used to incorporate the bone bridge 10 into the canine femur 100 is depicted in FIGS. 2A, 2B and 2C. FIG. 2A shows a canine femur 100 having a first femoral portion 104 and a second femoral portion 106 separated by a missing portion due to an osteotomy. The bone bridge 10 is inserted between the first and second femoral portions 104, 106, as shown in FIG. 2B. After the implant 10 has been positioned so that the notches 30 on the ends of the implant 10 are adjacent to the first and second femoral portions 104, 106, the bone bridge is stabilized. Stabilizing may be performed by using a bone plate 108 and bone screws 110 as shown in FIG. 2C, or may be done with any standard device suitable for stabilizing the implant 10 until bone tissue growth is sufficient to hold the implant 10 in place.

The osteoceramic material used for the bone bridge should contain at least 25 percent, and preferably about 50 percent calcium phosphates. The calcium phosphates should have a calcium to phosphate ratio within the range of about 1.0 to 2.00, which encompasses such compounds as hydroxyapatite, fluorapatite, oxyapatite, tricalcium phosphate and calcium pyrophosphate. The structure of the osteoceramic is like that of a sponge, where the skeleton of the sponge is an inert material such as spinel and the holes of the sponge are filled with calcium phosphates. Bone tissue will bond directly to the osteoceramic as it would to calcium phosphates, and the presence of the inert material provides enduring strength to the composite. Any suitable inert material may be used in place of spinel, so long as it is sufficiently insoluble so that it does not alter the local chemistry at the implant to tissue interface.

The surface geometry of the bone bridge 10 may be configured as necessary to achieve microstructural and anatomical continuity between the bone bridge 10 and the native bone tissue. This continuity is necessary so that new bone tissue will build the same local structure as that of the missing or damaged bone. For example, if the damaged bone is the diaphysis of the femur, which is a dense tube with a certain wall thickness, then the bone bridge 10 should also be dense and have a wall thickness 24 that is approximately the same as that of the damaged bone. The new bone tissue will then be dense bone and will be able to support the stresses normally placed on the diaphysis of the femur.

If the damaged bone is trabecular bone, then the outer surface 22 should have a plurality of web-like projections thereon. The individual bone trabeculum of the new bone growth can attach to the web-like projections, thereby integrating the bone bridge 10 more fully into the new bone growth. The web-like projections only need to be deep enough on the surface to allow the new bone tissue to conform and support the local stresses delivered to the trabeculae, and should not be excessively deep because that would weaken the implant. The microstructural continuity thereby achieved between the bone bridge 10 and the new and damaged bone tissue results in a continuity of stress across the rebuilt bone at the level of individual trabeculae.

Microstructural and anatomical continuity requires the bone bridge 10 and the native bone tissue at the site of the implant to have similar surface geometries, shape, and cross-sectional area. Continuity is especially critical for the load-bearing portions of the bone, so that the new bone tissue will have the strength and stress support that native bone tissue would have if the damaged bone were intact. Providing microstructural and anatomical continuity during tissue regrowth provides physical stresses to the new bone tissue that result in improved bone regrowth. Microstructural continuity is also critical for successful bonding of bone tissue directly to the implant.

Referring once more to FIG. 1, it can be seen that the bone bridge 10 has the shape of a hollow cylinder 20 with a first end 26 and a second end 28. At least one, and preferably both, of the first and second ends 26,28, is provided with a plurality of notches 30 sized to permit bone tissue ingrowth. The notches 30 may be tapered, preferably so that they are narrowest at the end of the cylinder 20 and wider toward the middle of the cylinder 20, yielding a key or dovetail shaped notch. These notches must be large enough to allow strong bone to form within them, and provision must be made for the blood supply necessary for the normal physiological processes of bone growth and bone repair to operate in the same way it does in the adjoining tissue. The growth of bone tissue into the notches 30 permits the bone bridge 10 to withstand tensile and torsional forces placed on the new bone. Bending stresses may also be accommodated by the growth of bone into the notches 30.

A preferred bone bridge 10 is shown in FIG. 1 to have a plurality of longitudinal grooves 32 in the outer surface of the cylinder 20. The grooves 32 may extend substantially along the entire length of the cylinder 20, and may be tapered. Preferably the grooves are outwardly tapered so that they are narrowest at an outermost portion of the outer surface. The grooves 32 may be radially aligned with the notches 30 to form a plurality of notched grooves in the outer surface. The grooves 32 should be large enough to permit bone ingrowth so that tensile and bending forces may be accommodated without displacement of the bone bridge 10.

The use of notches 30 with or without grooves 32 for bone tissue to grow into enables the new bone incorporating the bone bridge 10 to withstand tensile, torsional, bending and compressive forces normally placed on bones. In addition, the ingrowth of bone tissue mechanically fixes the bone bridge 10 in place. To facilitate bone ingrowth, the grooves 32 and notches 30 should be large enough to provide the type of normal, healthy bone normally present at the site.

The geometry of the bone bridge 10 should not interfere with the transport processes and cellular responses required for repair. For example, cement should not be injected into bone tissue, and natural blood and lymphatic service to the tissue should be maintained. The natural physiological response of wound healing, callus formation and remodeling must not be interfered with if the implant is to be successful. Preferably the bone bridge 10 is a hollow cylinder 20 to permit regeneration of medullar tissue inside the cylinder 20, and more preferably the osteoceramic material of the cylinder 20 has a plurality of perforations 34 in it to permit the passage of blood and lymph vessels from the inside of the cylinder 20 to the outer surface 22. These perforations 34 should be 200 microns or greater in diameter to permit the growth of Haversian systems through the perforations.

The structure of the bone bridge 10 as described above may be varied as required for a specific orthopedic application, but certain principles of implant design must be followed for the method of the present invention to be successful. First, the implant must be primarily osteoceramic or have osteoceramic surfaces in contact with native bone tissue. Second, the implant should have a tensile strength at least as strong as the bone it contacts. The strength should not depreciate in the host atmosphere. Third, the surgical procedure should be appropriate to the implant site, aseptic, without unnecessary trauma to the tissue, and provide temporary support for the implant. Fourth, the design of the implant should provide stress levels normal to the bone and allow for tensile, compressive, bending, and torsional loads. Shear stresses at the interface should be minimized. Fifth, the implant should not interfere with the normal internal and external processes associated with wound healing, recovery, and remodeling. Sixth, the surface geometry in contact with bone should be similar to that of the bone it contacts.

With reference to Example 1 below, a basic tubular implant shape, referred to as a bone bridge, was adopted to provide for normal healing. The wall thickness was the same as the cortical bone, so that the compressive stresses delivered to it would be the same as if the bone were continuous. (Several specimens were provided so that the surgeon could choose the appropriate one.) Tensile and torsional forces were accommodated by forming the end of the tube with dove-tailed recesses so that bone could grow into the recess. After the recesses were filled the bone could not be withdrawn, providing tensile force accommodation. Torsional stresses were also accommodated by the bone grown into the recesses. After the recesses were filled bending stresses also could be accommodated. However, it is critical that the bone maintain the bond with the implant. This was encouraged by a series of axial grooves on the outside of the implant, with radial holes conducting blood from the medulla to the grooves (FIG. 1). The net result looks like a splined tube. It can accommodate tensile, compressive, bending, and torsional loads. It does not interfere with wound healing, callus formation, and remodeling. This satisfies the physical design requirements.

Note that the structure of laminar bones is different from the structure of long bones. For laminar bones the primary blood supply is from an internal layer between the two external cortices. A prosthesis in laminar bone can have openings at the blood supply layer for rapid ingrowth into the openings. For example, to close a trephine hole in the skull the prosthesis could be an osteoceramic disk with a thickness similar to the skull thickness. It could have an external groove at the depth of the blood supply layer for bone ingrowth. It could have a flange to engage the exterior cortex of the bone to prevent penetration into the skull cavity. And it can be tapered slightly for easier insertion.

Note also that the muscles covering the skull can be used for fixation and that no bone plate is required for stabilization.

Joint Replacement

Figure 3:
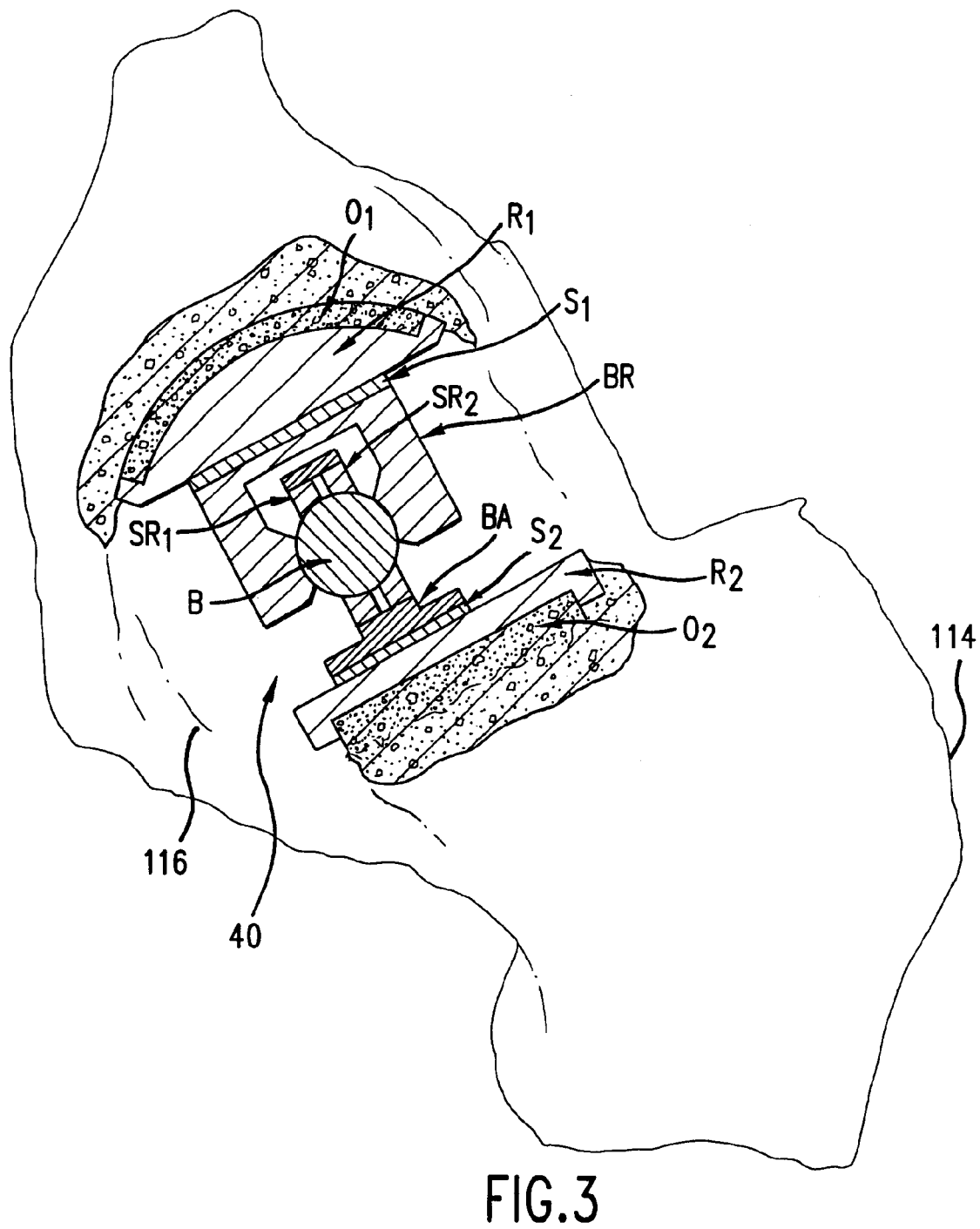
FIG. 3 is a partial sectional view of a total hip prosthesis used in the method of the present invention.

FIG. 3 depicts a joint replacement device 40, in this embodiment shown as an artificial hip, that is compatible with native bone tissue due to the use of osteoceramic material at the interface of the device 40 and native bone. The osteoceramic bodies $O_1, O_2$ contact the femur 114 and the acetabulum 116, and are structured so that new bone tissue may bond directly to the osteoceramic bodies $O_1, O_2$. This direct bonding stabilizes the joint replacement device 40, and obviates the progressive loosening of the acetabular or femoral components that occurs over time with known implants. The design of the joint replacement device 40 of the present invention also reduces or avoids the removal of healthy bone tissue during the joint replacement process.

The hip prosthesis shown in FIG. 3 is composed of four components: a sapphire ball and ring assembly, an osteoceramic tissue contact material $O_1, O_2$, a metal body that holds the bearing rings and the osteoceramic in place, and optionally a cage to prevent dislocation. For some modifications, the natural ligaments and tendons can be used to prevent dislocation. The body includes members to allow adjustment of position and angle, and is in two parts, an acetabular part $R_1$ and a femoral part $R_2$. The acetabular part $R_1$ provides for adjustment of the angle and thickness of the prosthesis. The femoral part $R_2$ has provision for a femoral stem extension that can be used if necessary. These components are discussed in turn.

The sapphire ball and ring assembly makes up the low-friction ball-and-cup portion of the prosthesis. That is composed of a sapphire ball B and two sapphire rings $SR_1, SR_2$. Sapphire is single-crystal aluminum oxide that is harder and stronger than polycrystalline aluminum oxide. It is chosen for its low friction and high strength because this makes it possible to use a much smaller ball than is possible with conventional ceramics. Because the ball B is smaller it does not require as much space, and this makes it possible to replace the hip without removing much tissue. The sapphire ball B fits into the area previously occupied by the femur ball and acetabulum, with provision that the center of rotation of the sapphire ball B and ring $SR_1$ is at the center of rotation of the joint being replaced. Another advantage of the sapphire ball B and ring $SR_1$ is that they can be made by inexpensive methods. It can be produced as rods and tubes that can be cut to provide stock for balls and rings, and is then machined to produce the bearing surface in the ring by simple rotational or automatic grinding and polishing. This does not require the expensive, computer-controlled milling and polishing operations required for known ceramic designs. The presence of two rings $SR_1, SR_2$ allows the bearing B surface to accommodate the kinematics of joint rotation with greater freedom and less friction. Note that ruby is colored sapphire and may also be used.

The osteoceramic tissue contact material is a great improvement over conventional prostheses because bone will bond to it, regenerating to hold it stable and prevent loosening. It is a brittle material that will fail if excessive tensile stresses are imposed. Therefore, it is employed in a way to minimize tensile stresses. It is shaped to provide projections, holes, notches or grooves, or combinations thereof, for bone to grow into and prevent movement. Provision for mechanical fixation is also provided, but the holes, notches or grooves may be provided with a key shape so that, once filled, the bone cannot be easily withdrawn. This provides tensile and rotational stability in addition to compressive stability. The osteoceramic is made as dense and strong as possible, but provision is made on the surface to have its surface structure similar to that of the bone it is attached to. In that way the normal physiological responses of the tissue can be used by the body to bond to the implant.

Referring to FIG. 3, the metal body of the acetabular component $R_1$ holds and supports the acetabular osteoceramic $O_1$. The osteoceramic $O_1$ can be pre-stressed with the metal body $R_1$. The surface of the acetabulum 116 is prepared by the surgeon to fit the proximal surface of the osteoceramic $O_1$. The surface of the osteoceramic $O_1$ contains key-ways or notches into which the bone of the acetabulum 116 can grow and fix the implant in place. Bone screws through the acetabular body component $R_1$ and the osteoceramic $O_1$ are not shown. Variations in geometry of the tissue contact surface to accommodate acetabular geometry are within the scope of this invention. Shims $S_1$ can be flat or tapered to adjust the center of rotation of the artificial joint 40 to its desired position. Fixed to the acetabular metal body $R_1$ is the sapphire bearing retainer BR that holds the sapphire ball bearing B in fixed position. The bearing B is held so that it cannot escape. Drilling a hole in the bearing and adding a bolt through the bearing into the two halves of the bearing retainer BR is also possible. The bearing retainer BR is relieved above and below the ball to provide for motion on an axis perpendicular to the plane of the drawing.

Riding on the ball B is a sapphire ring bearing assembly BA. It consists of a retainer that surrounds the two sapphire bearing rings $SR_1, SR_2$ that ride on the sapphire ball B. The sapphire bearing rings $SR_1, SR_2$ are polished to ride freely on the sapphire ball B, so that rotation about the horizontal axis in the plane of FIG. 3 is unrestricted. Modest rotation on the vertical axis in the plane of FIG. 3 is also possible, so the artificial joint 40 has the same degrees of freedom as a natural hip joint, e.g. abduction=40°. The bearing retainer BR accepts polished sapphire bearing rings $SR_1, SR_2$, one medial and one lateral to the ball B, with adjusting mechanisms so that they can be fastened firmly in place when the surgeon assembles the joint 40.

The bearing assembly BA is fastened to the femoral metal body component $R_2$. Shims $S_2$ of appropriate shape are provided to adjust the position of the femur to the center of rotation fixed by the position of the ball B. The femoral metal body component $R_2$ supports the osteoceramic $O_2$ in contact with the bone of the femur 114. The component $R_2$ can prestress the osteoceramic $O_2$ and it retains it in contact with the bone. Bone screws (not shown) provide for initial fixation of both the femoral metal body component $R_2$ and the osteoceramic $O_2$. The osteoceramic $O_2$ has microstructual continuity with the femur 114, such as surface projections to enhance fixation. Variations in geometry to accommodate femoral tissue structure are within the scope of this invention. A femoral intramedullary extension is also within the scope of this invention, and would be used if there is breakage of the femoral stem. The combined assembly BR, B, BA forms a cage which physically prevents dislocation of the artificial joint 40. Modifications of the geometry to improve this cage-like structure are possible and are included within the scope of this invention. It is also possible to use bearing cups or rings that are not rigidly held to the ball so that dislocation is prevented by the ligaments and tendons of the joint.

The surgical method used to incorporate the joint replacement device 40 into the skeletal structure of a human or animal varies according to the particular situation facing the surgeon. The joint replacement method of the present invention begins with the provision of a joint replacement device such as an artificial elbow or an artificial hip having osteoceramic bone contact surfaces. The surface geometries of the osteoceramic bone contact surfaces should be configured to match the surface geometries of the bones to which they are attached, so that tissue ingrowth and bonding directly to the joint replacement device is facilitated. Next, the joint replacement device is positioned in an orthopedically desirable position, and may then be stabilized by attaching the bone contact surfaces to the bones by means such as bone screws, sutures, wires or the like. Most importantly, the natural blood and lymphatic service to the bones must be maintained by reattaching or repositioning ligaments, blood vessels and the like which have been displaced or disconnected during the implanting procedure.

For example, the femoral component of the metal body part has provision for several different situations. In the case of an arthritic hip with strong, healthy ball and stem it is the articulating surfaces that must be replaced. Because of the small size of the sapphire ball and ring assembly it is possible to not remove the ball and stem of the femur. Only the proximal surface of the femoral ball must be removed. The femoral ball is reamed in a frustro-conical configuration so that the femoral osteoceramic component $O_2$ can be recessed into the head of the femoral ball, retaining the strong cortical exterior of the femoral ball to support it. The femoral body part $R_2$ has a component with a recess to hold the osteoceramic component $O_2$, providing radial containment. It can be pre-stressed to strengthen the osteoceramic. The proximal portion of the femoral body part $R_2$ supports the sapphire ring assembly BA. Provision is made for bone screws for fixation. Additional components for displacement and angular adjustment may be provided but are usually not required.

The first step in the surgical implantation of an artificial hip is to cut and ream the femoral ball for the femoral osteoceramic $O_z$ and to assemble the sapphire ring $SR_2$. (A metal jig with a metal ball fixed in place is used first for testing the kinematic alignment of the joint replacement device.) The acetabular osteoceramic component $O_1$ is fixed in place and the necessary extensions and angular adjustments are made to bring the sapphire ball B into position. Then the femoral jig is removed and the ring-bearing body component BA is fixed in place. The metal body components may be selected by the surgeon as the surgery progresses, thereby providing greater flexibility and ease in placing the osteoceramic components and meeting the kinematic and positional requirements.

During the implantation process, the surgeon removes the ligament at the head of the ball temporarily. After the prosthesis is in place, the surgeon reattaches the ligament to the femoral head at a position to provide blood to the oriented trabecula supporting the medial aspect of the femoral head. If the stem of the femur is not strong or if it is fractured it can be cut off and a conventional stem inserted into the medulla of the femur similar to the current practice of replacing the stem and head. However, osteoceramic can be used as the tissue interface material so that the bone tissue of the femur may bond directly to it to firmly hold the prosthesis in place. All such modifications for the support of the femoral component of the sapphire ring are included within the scope of this disclosure. The joint should not provide electrical contact between the acetabular and femoral body parts.

Guided Bone Repair Without Tissue Bonding to the Implant

FIGS. 4A through 4F depict a method of incorporating a bone guide 50 into the skeletal structure of a human or animal for inducing bone repair. The bone guide 50 is a rod or tube containing calcium phosphate, which preferably is non-loadbearing and which serves to guide the growth of new bone tissue. The bone guide or graft is preferably designed to loosely fit into the intramedullary cavities of the damaged bones, where it may be stabilized by bone screws, plates, wires or the like until sufficient bone tissue growth has occurred.

The net result is a graft in which the strength is provided by the natural bone, not the graft. The graft is preferably non-loadbearing, although it may participate in mechanical loading during the healing process. The graft serves as a guide for the bone repair and remodeling process by controlling the macrostructure of the bone response in accordance with the known macrostructure physiological repair mechanisms of the tissue and by chemically enhancing bone mineralization. In the end, it is possible for the bone graft to carry some mechanical load if the tissue response and the bone rebuilding incorporates some of its strength to the final, remodeled bone morphology. Whether or not it carries appreciable load will depend on the geometry at the implant site and the physiological repair responses of the bone itself.

Natural bone repair requires stabilization and vascularization. The source of blood supply after the initial hematoma and fibrous callous formation is internal through arterial structures and external from surrounding soft tissue, especially muscles. This blood is conducted through the endosteum and periosteum tissues. Known bone grafting methods often strip the periosteum when accessing the bone for internal stabilization and often injure this tissue during the original fracture and post-fracture manipulations. If the tissues do not regenerate, but join to themselves at the proximal and distal ends of the remaining bone, non-union occurs. This produces rounded ends enclosing cancerous bone, a typical non-union.

The present inventor has discovered that bone tissue regrowth can be guided if a calcium phosphate containing graft is provided so that the periosteum is prevented from joining around the periphery of the bone ends. Preferably, the endosteum is separated from the guide by a space sufficient so that the blood supply to the endosteum from the intramedullary cavity is maintained. By using a graft containing calcium phosphate, the rate of bone repair is enhanced and formation of a fibrous capsule is prevented. The bone healing, in effect, follows the exterior surfaces of the implant, but is usually separated from it. The implant induces bone repair.

Guided Tissue Recovery and Concomitant Stabilization

Members of the Avian class have skeletal features different from mammals because the Avians fly. All bones are thin-walled. The skeleton is fragile and many of the bones are hollow. Birds like cranes, swans, hawks and eagles often suffer fracture of the humerus. Because the humerus is hollow, little endosteal blood supply is available. The vascularity of the external soft tissue is limited, so these fractures heal slowly. The hollow nature makes it difficult to stabilize the fracture with an intermedullary nail. If metallic bone plates are used for stabilization, the wing is too heavy so the bird can no longer fly. Broken wings are often compound fractures with bone ends exposed. These are usually necrotic, so the ends proximal and distal to the fracture must be removed.

Figure 5:
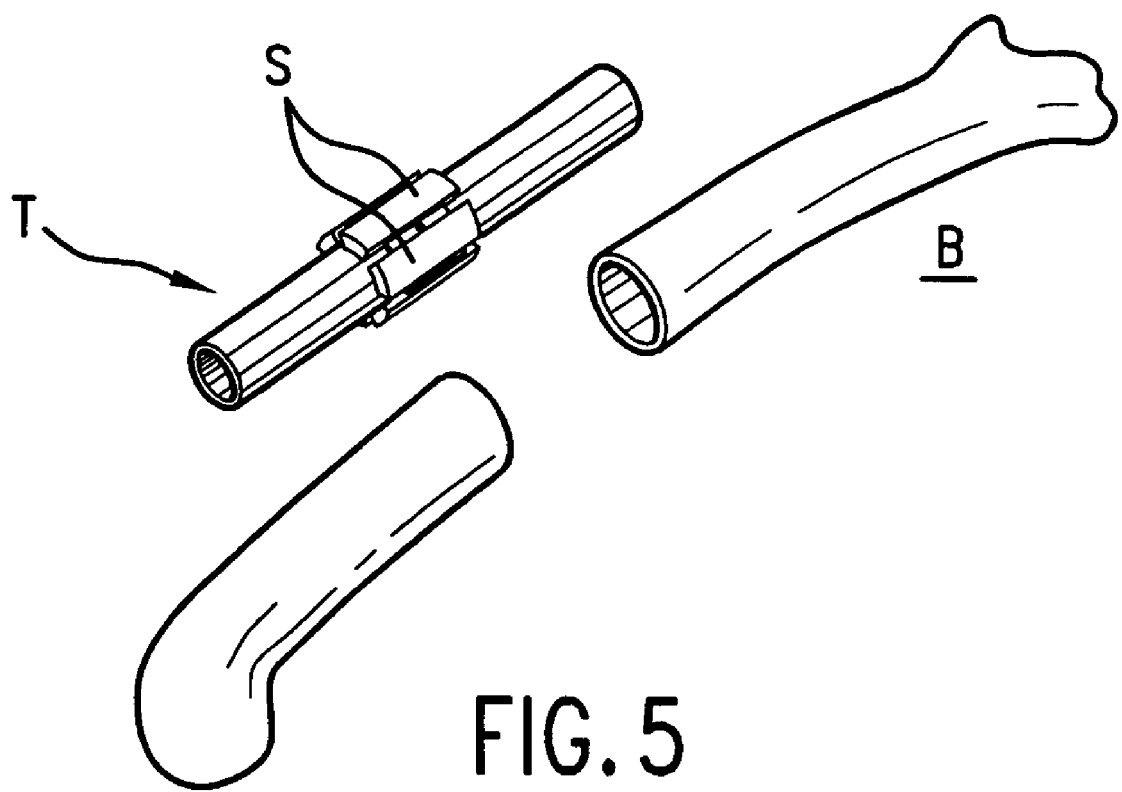
FIG. 5 is a perspective view of a combination guide tube and spacers for reconstruction of the humerus of an avian.

The method of bone reconstruction can be applied here: The osteoceramic can be used to stabilize the fracture and induce bone recovery. Its calcium phosphate nature enhances bone healing and callous formation and mineralization. A thin-walled tube of the same or similar thickness to the humerus wall is chosen of length sufficient to stabilize the fracture with an outside diameter just large enough to enter the open medulla of the proximal and distal bone, as shown in FIG. 5. If necessary, a spacer made of an osteoceramic material can be placed over the stabilizing tube, its length chosen to separate the proximal and distal ends of the bone to give the same length as the bone in the contralateral wing. It can be cemented or sutured in place on the osteoceramic stabilizing tube. The wall thickness of the spacer need only be thick enough to prevent the bone ends from sliding on the stabilizing tube. The fit of the stabilizing tube is critical. A selection of tubes of various diameters should be available. However, because of curvature and non-circularity of the bone a suitable diameter can be selected and cut to length. The surgeon stabilizes the fracture as described above and sutures the soft tissue to provide good vascular content with the original periosteum.

In the Avian example, an osteoceramic is used; the fracture is bridged by the implant; the fracture is stabilized; the geometry of the implant and its structure is the same as the adjacent bone, and the vascularity coming only external to the bone and implant assembly is accommodated. The stress level in the bone at the fracture site is within the range normally found in the bone. The tissue can repair itself bonding to the implant. By judicious selection of wall thickness and stabilizing tube length the bird will be able to fly when the bone remodeling is sufficient. Note that this example also provides a barrier for the healing periosteum to prevent closure on itself at the proximal and distal ends of the bone fracture. Note also that rotation on the longitudinal axis must be prevented during stabilization. The surgeon can prevent rotation by stabilizing tube fit or fixation with sutures engaging holes or notches in the tube ends.

Application of the teachings of the present invention to a specific problem or environment is within the capabilities of one having ordinary skill in the art in light of the teachings contained herein. Examples of the methods of the present invention appear in the following examples.

As demonstrated by the above disclosure and the following examples, the methods of restructuring bone according to the present invention are versatile and useful, particularly if certain preferred common elements to the embodiments and examples are followed, including:

1. A suitable surgical procedure for the application (sterility, anesthesia, approach, intervention and closure),
2. temporary stabilization to allow the tissue to respond in the way necessary for the application,
3. an implant containing calcium phosphate that enhances bone repair,
4. provision for the blood and lymph supply to allow the tissue to repair itself,
5. separation of any permanent bioinert materials from the bone by imposing a material having a calcium phosphate component between the bone and the bioinert material,
6. avoidance of exothermic reactions that cauterize tissue, and
7. avoidance of debris caused by wear or chemical breakdown.

For load-bearing implants, the tissue has a similar stress level to that of the tissue if the implant were not there, the geometry allows in-growth into large enough spaces to accommodate the tensile, compressive, bending and torsional loads that will be imposed, and the surface structure is similar to the structure of the bone at the implant site. The implant can also perform the initial stabilization, as in the case of the Avians.

For guiding implants, the implant enhances bone recovery and remodeling by its chemical nature and serves as a barrier to unwanted non-union, at the same time allowing for vascularization. This is not the same as a scaffold for bone mineralization. In fact, it is preferable to separate the bone from the implant to provide for the necessary blood supply, a direct opposite of the scaffold approach.

For joint replacement, the method of bone restructuring according to the invention requires less removal of bone because the tissue will bond to the osteoceramic interface, because the choice of a sapphire or ruby ball allows a smaller articulating component with simple rotational machining in its preparation, and because the metal components are isolated from hard tissue contact.

For all of these preferred embodiments, the physiological restructuring of bone is manipulated so that the bone will repair itself, either by bonding to the implant or by being guided by the implant. Existing implants violate most of the methods disclosed here for the restructuring of bone. This new method of restructuring bone is urgently needed in orthopedic surgery.

EXAMPLE 1

Surgical Procedure for Implanting Osteoceramic Bone Bridge

Anesthesia was induced with intravenous thiamylal sodium (17.5 mg/kg) and maintained with 1–3% halothane gas. Cephalothin sodium was administered pre and post surgical procedure as an antibiotic (20 mg/kg). The rear quarter of the dog was clipped and prepped using alternately Betadine and 95% alcohol. A 5-min sterile scrub with Betadine was performed following the initial preparation. The ECG was monitored. The leg was draped using aseptic technique and covered with a sterile stockingette.

A skin incision was made along the cranial border of the biceps femoris muscle from the level of the greater trochanter to the proximal patella. The skin was sewn to the stockinette using 2/0 monofilament nylon. Electrocautery was used to help provide hemostasis. The skin margins were retracted and the fascia lata was incised along the cranial border of the biceps femoris muscle. The biceps femoris was retracted caudally and the vastus laterus muscle was retracted cranially to expose the shaft of the femur. An 8-hole 316 L stainless steel compression plate was contoured to the lateral aspect at the center of the femur for later use. A section of the adductor muscles, which insert on the caudal aspect of the femur, was elevated at middiaphysis. The vastus intermedius was retracted from the cranial aspect of the femur at the same level. Two transverse osteotomies were then made with an oscillating saw, as shown in FIG. 2A. Each was approximately 12 mm from the midshaft. The diameter and the length of the osteotomy were measured, and an implant was selected of the same length and cortex thickness, as shown in FIG. 2B.

The implant was secured to the contoured plate with Kirschner wire, as shown in FIG. 2C. The plate was clamped to the lateral aspect of the femur to oppose the proximal and distal osteotomy sites to the ends of the implant. Three 3.5-mm cortical screws were placed on each side of the implant. The first screws on each side were aligned with a guide to produce compression of the bone to the implant. The area was irrigated with saline. The facia latera was closed with 0 monofilament polyglyconite sutures. The subcutaneous fat and fascia were closed with 2/0 monofilament nylon sutures. The skin was apposed with 4/0 surgical steel sutures. Cefadroxil (10 mg/kg per dose) was given twice a day for 6 days. The steel sutures were removed after 10 days.

The stainless steel compression plate was fixed to the proximal and distal bone plate. The compression of the bone to the ends of the plate brought the bone tightly to the ends of the implant, so that flexing of the plate would deliver compressive stresses to the ends of the implant. The bone plate was positioned laterally so that the normal bending stresses of load bearing would produce tension in the bone plate. This method of fixation satisfies the requirement that the implant be stabilized while wound healing and remodeling occur. Note that the movement that develops with time as the mechanical fixation of the bone plate deteriorates allows the bone to gradually accept the stresses imposed on the tissue/implant interface. The tissue remodels to accept the forces previously delivered to the bone plate.

The osteoceramic was formed as a dense tube with the same wall thickness and external (and internal) diameters as the cortical bone. This satisfies the important requirement that the implant should have microstructural continuity with the bone, and automatically assures that the stresses in the bone and in the implant are the same. The tissue remodels to support the implant in the normal range of stress that it would have if the implant were not present and bone was present instead.

The ends of the implant were provided with radial, tapered key-ways, as shown in FIG. 1. After bone grew into the key-ways the taper prevented the keys from being withdrawn, providing tensile strength to the bone/implant assembly. Longitudinal grooves were provided so that bone could bridge completely across the implant lying in the grooves and contribute additional tensile and bending strength. Since bone remodels to accommodate stress the density and thickness of the bone at the root of the keyway and in the grooves could be adjusted by the tissue to maintain structural integrity. The compressive stresses were taken at the projected area of the tissue at the value normally present because the diameter and the thickness of the tube was the same as the cortical bone. Torsional stresses were accommodated by the same structure as described for tension. Thus, the implant geometry satisfies the requirement that the forces imposed can be accommodated by the tissue.

At mid-diaphysis the blood supply for bone remodeling is provided by vascularization of the medulla and from the surrounding muscles. These supply the endosteum and periosteum respectively. The medullar supply could regenerate through the axial hole of the implant. Both endosteum and periosteum had their normal blood supply so that the normal physiological responses could generate and maintain healthy bone in the key ways. Radial holes were also provided connecting the axial hole to the longitudinal grooves, as shown in FIG. 1. This provides blood supply to the bone in the grooves making it possible for the tensile tissue in the grooves to generate and remain healthy. These provisions satisfy the requirement that the physiological and anatomical processes can operate normally to provide for healthy attachment to the implant.

This procedure produced an implant that was in compression at the ends, the bone plate taking the tension forces in bending and pulling. After wound healing took place the bone began to attach to the implant. The bone plate provides a resistance to bending loads. The edges of the bone plate, held tightly against the periosteum by the bone screws, cut through the periosteum and interfered with the external blood flow at that location, producing a weaker bone under the bone plate. The bone plate and the bone screws are walled off by the foreign-body capsule in such a way that movement becomes possible with time. The compressive and tensile loads gradually shift to the implant as the tissue responds to the stress stimulus, gradually taking more of the load. This can be observed radiographically as the bone fills the dovetail recesses and the longitudinal recesses. After about 1 year the bone plate was removed in a second surgical procedure. Enough stress had been transferred to the implant so that the bone plate was no longer necessary. The weak area under the plate was sufficiently local that fracture did not occur. The bone continued to remodel over 4 months. Eight years after removal of the bone plate the dog was active, continuing to stress the implant normally without evidence of pain or gait variations. Recent force plate measurements showed no significant difference between the force imposed on the operated and the contralateral limb. No further changes in remodeling occurred. It is believed the longitudinal recesses are completely filled with bone.

EXAMPLE 2

Use of an Osteoceramic Bone Guide to Stimulate Bone Growth

A length of bone two and one half times the diameter was removed from the diaphysis of a dog's femur. A tubular bone graft made from a composite ceramic, 50% calcium phosphate and 50% spinel, was inserted loosely into the medullar space, extending into the proximal and distal medulla of the adjacent bone ends; and a bone plate and screws was used to stabilize the bone. The screws holding the plate also restricted the axial displacement of the graft. (FIG. 4) The tube was enclosed by a massive hematoma that became fibrous and immobilized the free-floating bone graft within about 24 hours. There was sufficient space between the endosteum and the implant so that vascularization of the endosteum from the medulla was possible. Regeneration of blood and nerves through the axial core of the tube was also possible so that blood could be supplied to the endosteum at both ends of the graft. Note that radial holes connecting the axial core space with the outer surface of the graft could be provided if necessary. The exterior of the callous and the re-generation of the periosteum was provided with blood supply from the surrounding muscle. The periosteum at the proximal and distal ends of the ostectomy could not close on itself and produce hemispherical ends to the proximal and distal bone because the bone graft is interposed.

Figure 4A:
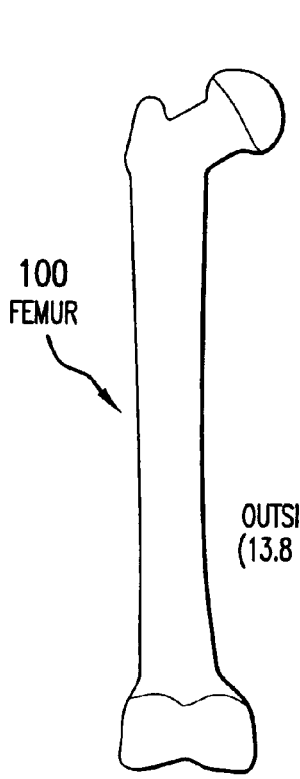
FIGS. 4A, 4B, and 4C are a series of front elevational views of a femur illustrating a surgical procedure used in the present invention.
Figure 4B:
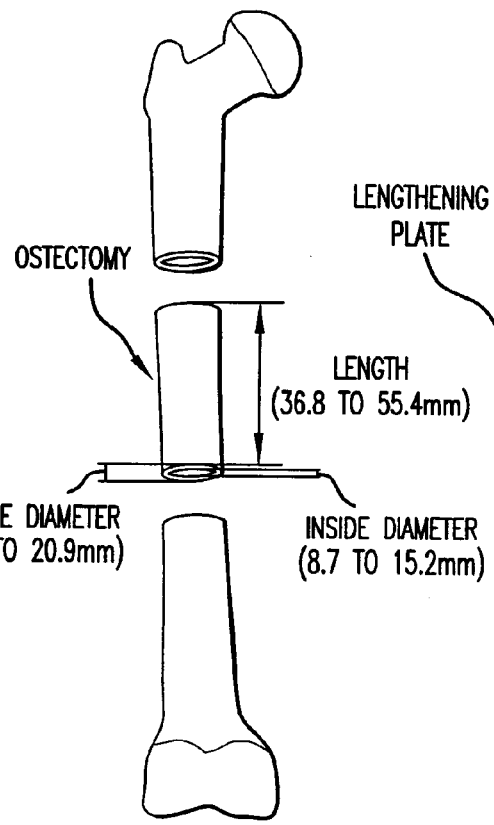
Figure 4C:
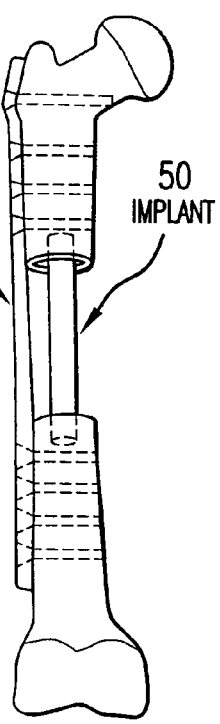
Figure 4D:
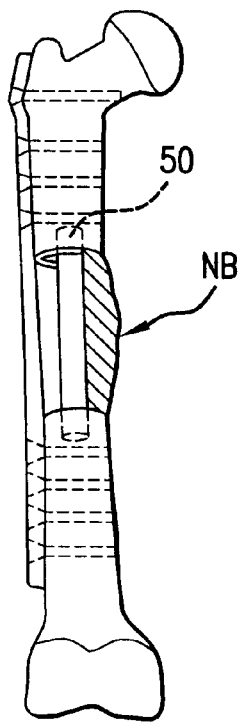
FIGS. 4D, 4E, and 4F are a series of front elevational views corresponding to FIG. 4C showing the new bone at 10 weeks and 35 weeks after surgery, and at 35 weeks after removal of the bone plate.
Figure 4E:
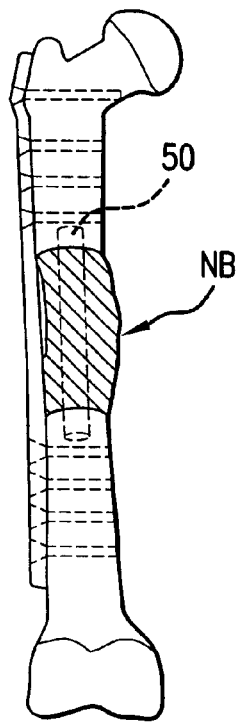
Figure 4F:
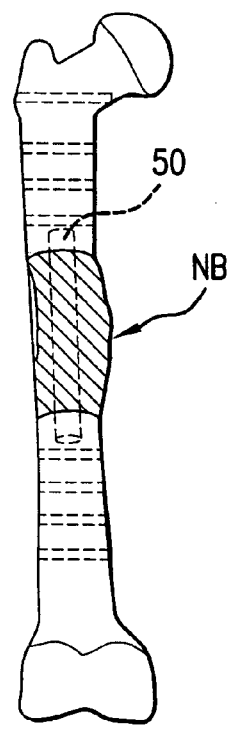

Bone regeneration was followed radiologically. After ten weeks bone was visible medially by radiograph. As shown in FIG. 4D, where microstrain occurred the bone mineralized, as the result of the calcium and phosphate ions released by the implant, and as a result of the micromotion. Over the next few weeks the new bone increased in density and extent until it encapsulated the tubular graft. As shown in FIG. 4E, the tissue gradually accepted more and more of the loads imposed by standing, walking and jumping as it became stronger. After 35 weeks the bone plate was removed. As shown in FIG. 4F, further remodeling occurred with time allowing the regenerated and remodeled bone to bridge the gap and provide strength. The graft does not need to be strong enough to support the limb, nor provide much strength after the remodeling is complete. Note that other configurations containing calcium phosphate could be used and are included in the scope of this invention. Note also that the shape of the graft must be designed in such a way as to provide for the requirements of stress level within the remodeled bone, the physiological responses (vascularity, barrier to endosteal or periosteal joining), rigidity, micromotion and chemical composition (release of $Ca^{2+}$ and $PO_4^{3-}$ ions).

The above description, drawings and examples are only illustrative of preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method of incorporating a prosthetic device into the skeletal structure of a human or animal for inducing bone repair and stabilizing a first and a second portion of damaged bone, comprising the steps of:

providing an osteoceramic cylinder adapted to tightly fit into the intramedullary cavity of the damaged bone;

positioning the osteoceramic cylinder inside the intramedullary cavities of the first and the second portions of damaged bone; and stabilizing the osteoceramic cylinder relative to the first and second portions of damaged bone.

2. The method of claim 1, wherein said step of stabilizing the osteoceramic cylinder further comprises positioning osteoceramic spacers on the outer surface of the osteoceramic cylinder.

3. The method of claim 1, wherein said step of stabilizing the osteoceramic cylinder further comprises connecting the osteoceramic cylinder to at least one of the first and second portions of damaged bone with one or more bone attachment means.

4. The method of claim 1, wherein the animal is an avian and the cylinder is hollow.

* * * * *